(12) United States Patent
Yamakoshi et al.

(10) Patent No.: US 7,083,573 B2
(45) Date of Patent: Aug. 1, 2006

(54) CUFF OF WRIST-MOUNT BLOOD PRESSURE MONITOR

(75) Inventors: Ken-Ichi Yamakoshi, Kanazawa (JP); Tomonori Inoue, Kyoto (JP); Takahide Tanaka, Otsu (JP); Yoshihiko Sano, Kyoto (JP); Shojiro Oku, Itabashi (JP)

(73) Assignee: Omron Corporation (JP)

( * ) Notice: Subject to any disclaimer, the term of this patent is extended or adjusted under 35 U.S.C. 154(b) by 5 days.

(21) Appl. No.: 10/447,281

(22) Filed: May 29, 2003

(65) Prior Publication Data

US 2004/0010198 A1 Jan. 15, 2004

(30) Foreign Application Priority Data

Jun. 3, 2002 (JP) .............................. 2002-161558

(51) Int. Cl.
*A61B 5/05* (2006.01)
(52) U.S. Cl. .................. 600/485; 600/500; 600/503
(58) Field of Classification Search ............... 600/485, 600/490, 493–496, 499–503; 606/202; 602/13
See application file for complete search history.

(56) References Cited

U.S. PATENT DOCUMENTS

| | | | | |
|---|---|---|---|---|
| 3,580,248 | A * | 5/1971 | Larson | 602/12 |
| 4,202,347 | A | 5/1980 | Sacks | |
| 4,429,700 | A * | 2/1984 | Thees et al. | 600/494 |
| 4,549,550 | A * | 10/1985 | Kami | 600/499 |
| 4,790,325 | A * | 12/1988 | Lee | 600/490 |
| 5,152,302 | A * | 10/1992 | Fareed | 128/878 |
| 6,336,901 | B1 * | 1/2002 | Itonaga et al. | 600/499 |
| 6,558,335 | B1 * | 5/2003 | Thede | 600/503 |

FOREIGN PATENT DOCUMENTS

| | | |
|---|---|---|
| DE | 2837707 | 3/1980 |
| EP | 1 013 220 | 6/2000 |
| FR | 1434168 | 4/1966 |
| JP | 64-72726 | 3/1989 |
| JP | 4-193259 | 7/1992 |
| JP | 9-224916 | 9/1997 |
| WO | WO 96/25110 | 8/1996 |

OTHER PUBLICATIONS

K. Nakamura, "Presented Papers," Conference of Horuriku Branch, Japanese Society for Medical and Biological Engineering, Dec. 8, 2001. (Japanese Cocument with Summary/Abstract).
European Office Action dated Oct. 1, 2004, issued in counterpart EP Application No. 03 011 847.5.
European Office Action dated Oct. 20, 2005, directed to corresponding EP Application No. 03011847.5

* cited by examiner

Primary Examiner—Robert L. Nasser
(74) Attorney, Agent, or Firm—Morrison & Foerster LLP

(57) ABSTRACT

A cuff of a wrist-mount blood pressure monitor includes an inflatable bag to which a predetermined quantity of fluid is supplied in order to press predetermined artery of a wrist, and a fixing member for mounting the inflatable bag on the wrist. The fixing member has a first half split ring-shaped fixing tool and a second half split ring-shaped fixing tool having an approximately ring shape with rigidity for preventing elastic deformation in a state where the inflatable bag is inflated.

3 Claims, 10 Drawing Sheets (A)

(A)

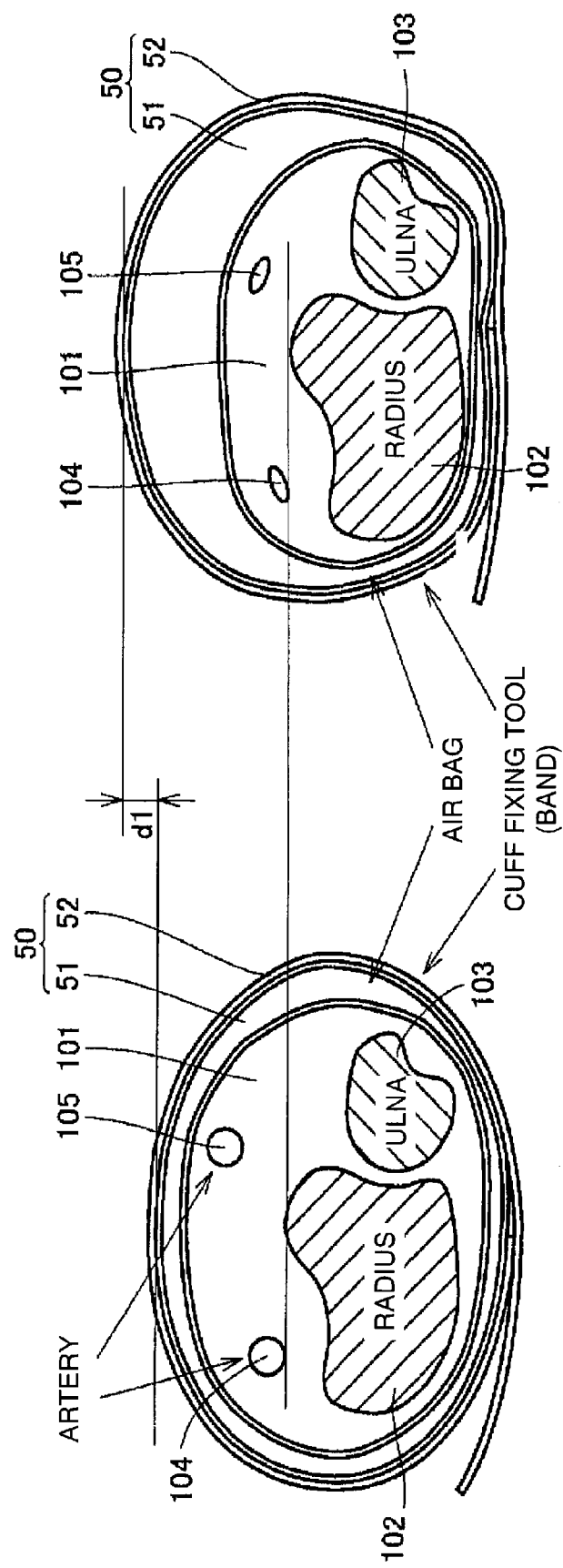

CUFF OF WRIST-MOUNT BLOOD PRESSURE MONITOR

BACKGROUND OF THE INVENTION

1. Field of the Invention

The present invention relates to a cuff of a wrist-mount blood pressure monitor which is used in a blood pressure monitor which is mounted on the body of a subject so as to measure blood pressure and, more particularly, to a structure of the cuff of a wrist-mount blood pressure monitor used in a wrist-mount blood pressure monitor for monitoring the blood pressure on the wrist.

2. Description of the Related Art

In general, the cuff of the wrist-mount blood pressure monitor to be used in a wrist-mount blood pressure monitor is composed of an inflatable bag into which a fluid such as air is supplied, and a fixing member to be mounted on a portion of a subject. After the inflatable bag is mounted on the wrist by using the fixing member, gas such as air is supplied to the inflatable bag, so that the artery of the subject is pressed and blood pressure is measured at a pressuring process or an exhaust process of the inflatable bag. As the fixing member, a band type cuff band, a holding elastic plate disclosed in Japanese Patent Application Laid-Open No. 9-224916 (1997) or the like can be used.

In the prior cuff of the wrist-mount blood pressure monitor having the above structure, however, since the fixing member is composed of a member with elasticity from a viewpoint of facilitation or the like of the mounting on the wrist, there arises a problem that the fixing member stretches and is deformed according to expansion of the inflatable bag. This problem will be explained with reference to FIGS. 10A and 10B.

FIGS. 10A and 10B are diagrams showing a cross section of a wrist, and FIG. 10A shows a state before the inflatable bag 51 is inflated, and FIG. 10B shows a state where the inflatable bag 51 is inflated. As shown in FIG. 10A, the cuff of the wrist-mount blood pressure monitor 50, which is composed of the inflatable bag 51 and a band-type cuff band 52 as the fixing member, is wound around the wrist 101. As shown in FIG. 10B, the inflatable bag 51 is then inflated, so that radial artery 104 in a vicinity of a radius 102 and ulnar artery 105 in a vicinity of an ulna 103 are pressed.

Since the cuff band 52 is, however, composed of the member with elasticity, the inflatable bag 51 inflates to the side of the wrist 101, and the cuff band 52 stretches and deforms so that the inflatable bag 51 inflates greatly to a direction separating from the wrist 101. At this time, as shown in FIGS. 10A and 10B, a distance (d1) from the radius 102 to the cuff band 52 increases. That the distance (d1) is large means that it is necessary to largely inflate the inflatable bag 51 in order to press the wrist 101. For this reason, a flow rate of an air pump for inflating the inflatable bag 51 should be increased, and thus it is difficult to miniaturize the air pump.

Although a tension is generated in the inflatable bag 51 according to its expansion, as the inflatable bag 51 inflates more largely, the tension to be generated becomes stronger, thus deteriorating efficiency of pressure transmission to a blood vessel wall to be pressed. A phenomenon such that the pressure to be transmitted to the blood vessel wall to be pressed (blood pressure of blood vessel inner wall to be pressed) is stronger than internal pressure in the air bag, therefore, occurs, and thus there also arises a problem that the blood pressure cannot be measured properly.

The measuring principle of an oscillometric method is established under the presumption that the pressure of the blood vessel inner wall to be pressed is equal with the pressure in the inflatable bag, and thus the pressure of the blood vessel inner wall to be pressed is estimated to be the pressure in he pressing fluid bag. For this reason, when the pressing force of the blood vessel to be pressed becomes insufficient, the pressure in the inflatable bag becomes higher than the pressure of the blood vessel inner wall to be pressed at the time when the blood vessel to be pressed is broken, and the blood pressure is measured high.

As the fixing member, there are a method of winding an elastic plate harder than the cuff band around the wrist and a method of connecting a plurality of curved covers via hinges and winding them around the wrist. Since they, however, use an elastic member as a material or a fastening method, the above-mentioned problems arise.

SUMMARY OF THE INVENTION

The present invention is devised in order to solve the above problems, and its object is to provide a cuff of a wrist-mount blood pressure monitor which adopts a fixing member for making an inflating direction of an inflatable bag to face a wrist so as to enable an air pump to be miniaturized and blood pressure measuring accuracy to be improved.

A cuff of a wrist-mount blood pressure monitor according to the present invention includes: an inflatable bag to which a predetermined quantity of fluid is supplied in order to press artery of a wrist; and a fixing member for mounting the inflatable bag on the wrist, wherein the fixing member includes: a substantially ring-shaped fixing tool having an opening end including a predetermined gap area, holding the inflatable bag on an inner side of the opening end, and having rigidity for preventing elastic deformation in a state where the inflatable bag is inflated; and a damper for clamping the fixing tool on the wrist in a state where the fixing tool is mounted on the wrist.

With this structure, even in the state where the inflatable bag is inflated, the fixing tool is not elastically deformed, so that the most part of pressing force caused by the expansion of the inflatable bag contributes to pressure for pressing artery of the wrist. As a result, since a capacity of the inflatable bag is miniaturized, a necessary air flow rate can be reduced, so that the miniaturization of an air pump can be realized. Reduction in an expansion quantity of the inflatable bag suppresses tension generated in the inflatable bag to be small, so that accurate blood pressure measurement can be realized.

In the cuff of a wrist-mount blood pressure monitor, an inner surface of the fixing tool preferably has a dent portion for preventing contact with a processus styloideus ulnae. The dent portion includes a recess which is provided on an area corresponding to the contact portion with the processus styloideus ulnae, a through hole (opening area), and a portion such as the recess or the through hole filled with a soft material such as sponge. Since the fixing tool of the present invention is not elastically deformed, when the fixing tool is mounted on the wrist, the fixing tool comes in contact with the processus styloideus ulnae, and thus it is considered that the processus styloideus ulnae aches. The dent portion for avoiding the contact with the processus styloideus ulnae is, therefore, provided, so that the fixing tool is avoided contacting with the processus styloideus ulnae, and the cuff of the wrist-mount blood pressure monitor can be mounted on the wrist comfortably. The processus styloideus ulnae is fitted into the dent portion, so that locating of the cuff of the wrist-mount blood pressure monitor with respect to the wrist can be realized.

BRIEF DESCRIPTION OF THE DRAWINGS

FIGS. 10A and 10B are diagrams showing a state where the cuff for the wrist-mount blood pressure monitor 50 is mounted on the wrist 101 in a prior art.

DESCRIPTION OF THE PREFERRED EMBODIMENTS

The embodiments of a cuff of a wrist-mount blood pressure monitor of the present invention will be explained below with reference to the drawings.

First Embodiment (Structure of the Cuff of the Wrist-Mount Blood Pressure Monitor 10)

Figure 1:
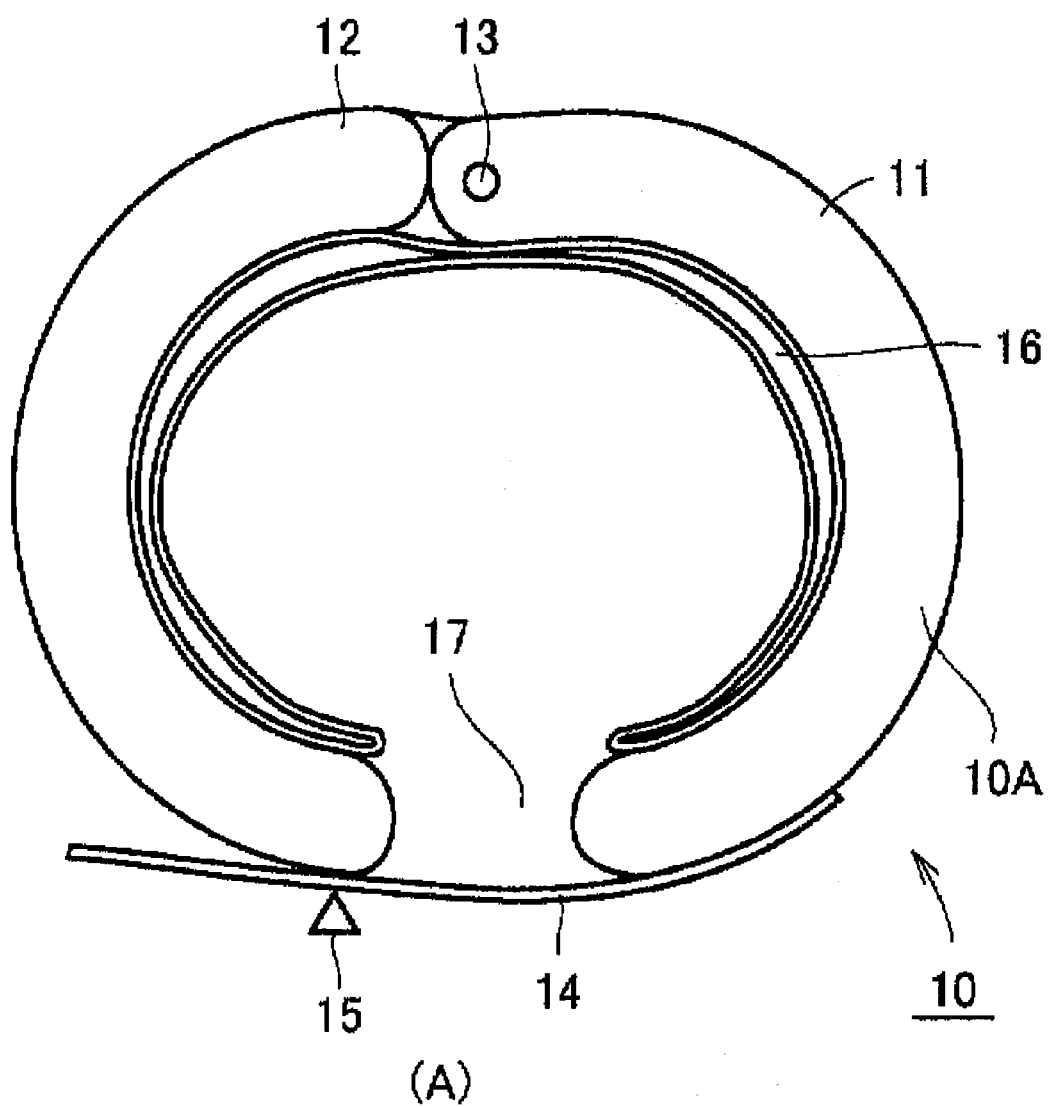
FIG. 1 is a sectional view showing a structure of a cuff of a wrist-mount blood pressure monitor 10 according to the first embodiment of the present invention.
Figure 2:
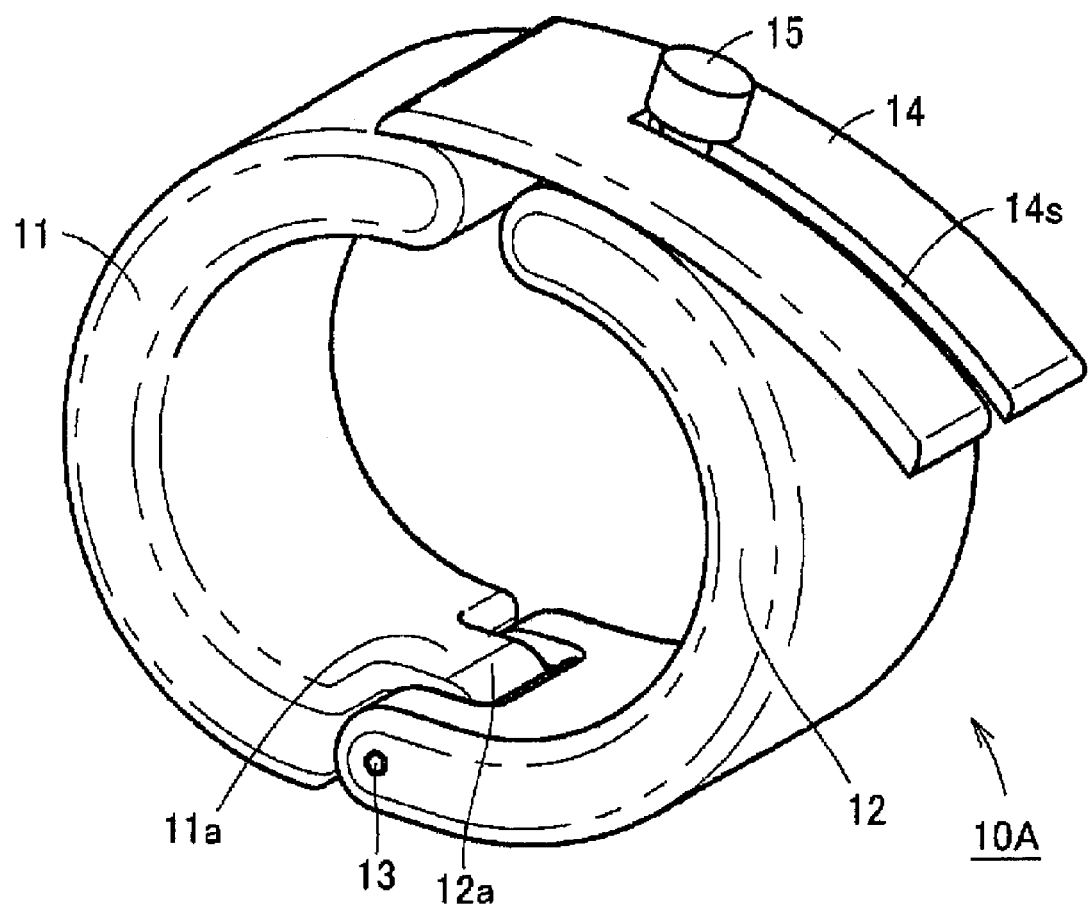
FIG. 2 is a whole perspective view showing only a structure of a fixing member 10A of the cuff of the wrist-mount blood pressure monitor 10 according to the first embodiment of the present invention.

A structure of the cuff of the wrist-mount blood pressure monitor 10 according to the embodiment of the present invention is explained with reference to FIGS. 1 and 2. FIG. 1 is a sectional view showing the structure of the cuff of the wrist-mount blood pressure monitor 10, and FIG. 2 is a whole perspective view showing only a structure of a fixing member 10A of the cuff of the wrist-mount blood pressure monitor 10.

With reference to these drawings, the cuff of the wrist-mount blood pressure monitor 10 has an inflatable bag 16 to which a predetermined quantity of fluid is supplied in order to press predetermined artery of a wrist, and the fixing member 10A for mounting the inflatable bag 16 on the wrist. The fixing member 10A has a first half split ring-shaped fixing tool 11 and a second half split ring-shaped fixing tool 12 having an approximately ring shape which are not elastically deformed in a state where the inflatable bag 16 is inflated. As a material of the first half split ring-shaped fixing tool 11 and the second half split ring-shaped fixing tool 12, acrylic resin, ABS resin or the other thermoplastic, metal or the like with a thickness of about 1 mm to 20 mm is used.

One end of the first half split ring-shaped fixing tool 11 has a convex area 11a, and one end of the second half split ring-shaped fixing tool 12 has a dent portion 12a for receiving the convex area 11a so that they are connected by a hinge 13 in a turnable state.

The other end of the first half split ring-shaped fixing tool 11 has a rail 14 with a slit 14s and the other end of the second half split ring-shaped fixing tool 12 has a clamping screw 15 which slides along the slit 14a and fixing the sliding with respect to the rail 14 due to clamping as a damper for clamping the fixing member 10A to the wrist in the state where the fixing member 10A is mounted on the wrist. The rail 14 is also prevented from elastically deforming.

An opening end 17 composed of a predetermined gap area is provided on the side at the other ends of the first half split ring-shaped fixing tool 11 and the second half split ring-shaped fixing tool 12 from a viewpoint of correspondence to wrist having various thickness.

(Mounting State and Working Effect)

Figures 3A, 3B:
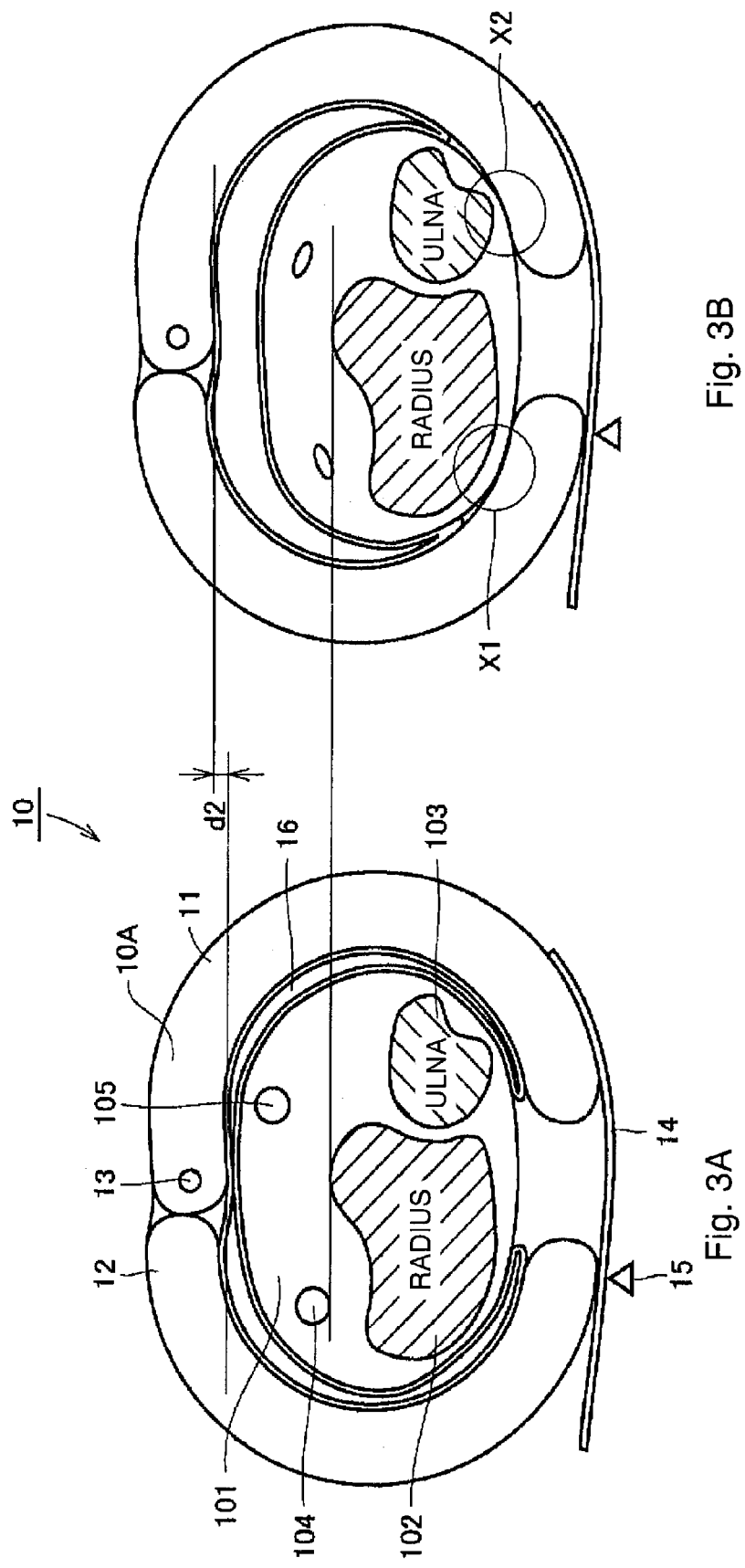
FIGS. 3A and 3B are diagrams showing a state where the cuff of the wrist-mount blood pressure monitor 10 is mounted on a wrist 101 according to the first embodiment of the present invention.

FIGS. 3A and 3B show a state where the cuff of the wrist-mount blood pressure monitor 10 having the above structure is mounted on the wrist 101. FIG. 3A shows the state before the inflatable bag 16 inflates, and FIG. 3B shows the state where the inflatable bag 16 inflates.

When the inflatable bag 16 is inflated, a force is applied from the inflatable bag 16 so that the first half split ring-shaped fixing tool 11 and the second half split ring-shaped fixing tool 12 are widened outward in the cuff of the wrist-mount blood pressure monitor 10. The first half split ring-shaped fixing tool 11 and the second half split ring-shaped fixing tool 12 are not, however, deformed, and the ends of the first half split ring-shaped fixing tool 11 and the second half split ring-shaped fixing tool 12 come in contact with a radius 102 and an ulna 103 so as to holds the wrist 101 sufficiently (in FIG. 3B, areas surrounded by X1 and X2). As a result, as shown in FIGS. 3A and 3B, a distance (d2) between the radius 102 and the fixing tool can be smaller than the distance (d1) shown in FIGS. 10A and 10B.

That is to say, the most part of the pressing force generated by the expansion of the inflatable bag 16 contributes to pressure for pressing the artery of the wrist 101. As a result, the capacity of the inflatable bag 16 is miniaturized, and thus a necessary air flow rate is reduced, so that miniaturization of an air pump can be realized. The miniaturization of the inflatable bag 16 suppresses the tension generated in the inflatable bag 16 to be small, so that the accurate measurement of the blood pressure can be realized.

The cuff of the wrist-mount blood pressure monitor 10 can be mounted in the state where the first half split ring-shaped fixing tool 11 and the second half split ring-shaped fixing tool 12 are widened largely, so that convenience of the mounting of the cuff of the wrist-mount blood pressure monitor 10 on the wrist 101 can be improved. Since the first half split ring-shaped fixing tool 11 and the second half split ring-shaped fixing tool 12 can be turned each other, they can easily cope with the thickness of the wrist.

Second Embodiment

Figure 4:
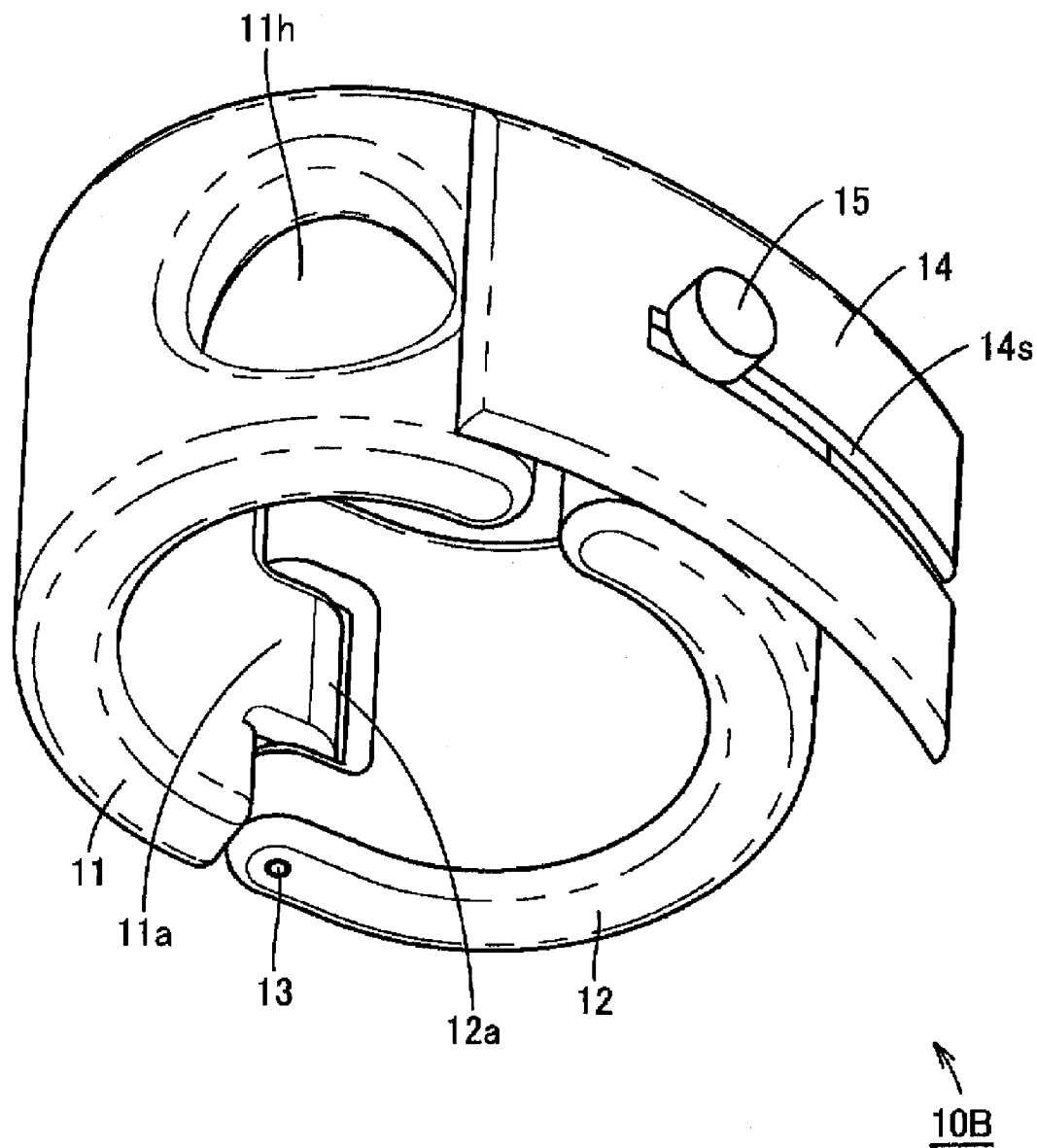
FIG. 4 is a whole perspective view showing only a structure of the fixing member 10B of the cuff of the wrist-mount blood pressure monitor according to the second embodiment of the present invention.

Since the characteristics of the cuff of the wrist-mount blood pressure monitor in this embodiment is the structure of the fixing member, only the structure of the fixing member will be explained. The other parts of the structure are the same as the structure of the cuff of the wrist-mount blood pressure monitor 10 in the first embodiment. The structure of the fixing member 10B is explained with reference to FIG. 4. FIG. 4 is a whole perspective view showing the structure of the fixing member 10B.

(Structure of the Fixing Member 10B)

When the fixing member 10B in this embodiment is compared with the structure of the fixing member 10A in the first embodiment, a predetermined area of the first half split ring-shaped fixing tool 11 has an opening area 11*h* for avoiding contact with a processus styloideus ulnae of the wrist. The other parts of the structure are the same as the structure of the fixing member 10A.

(Working Effect)

The cuff of the wrist-mount blood pressure monitor using the fixing member 10B in the present embodiment can also produce the working effect similar to that in the first embodiment. Since the first half split ring-shaped fixing tool 11 of this embodiment is not elastically deformed, when the first half split ring-shaped fixing tool 11 is mounted on the wrist 101, the first half split ring-shaped fixing tool 11 comes in contact with the processus styloideus ulnae, and thus it is considered that the processus styloideus ulnae aches.

When the opening area 11*h* for avoiding the contact with the processus styloideus ulnae is, therefore, provided, the first half split ring-shaped fixing tool 11 avoids contacting with the processus styloideus ulnae, so that the cuff of the wrist-mount blood pressure monitor can be mounted on the wrist 101 comfortably. When the processus styloideus ulnae is fitted into the opening area 11*h*, locating of the cuff of the wrist-mount pressure blood monitor with respect to the wrist 101 can be also realized.

In this embodiment, the opening area 11*h* is provided on the first half split ring-shaped fixing tool 11, but such an area is not limited to the opening area, and a dent portion for avoiding the contact with the processus styloideus ulnae may be provided on an inner surface of the first half split ring-shaped fixing tool 11.

Third Embodiment

Figure 5:
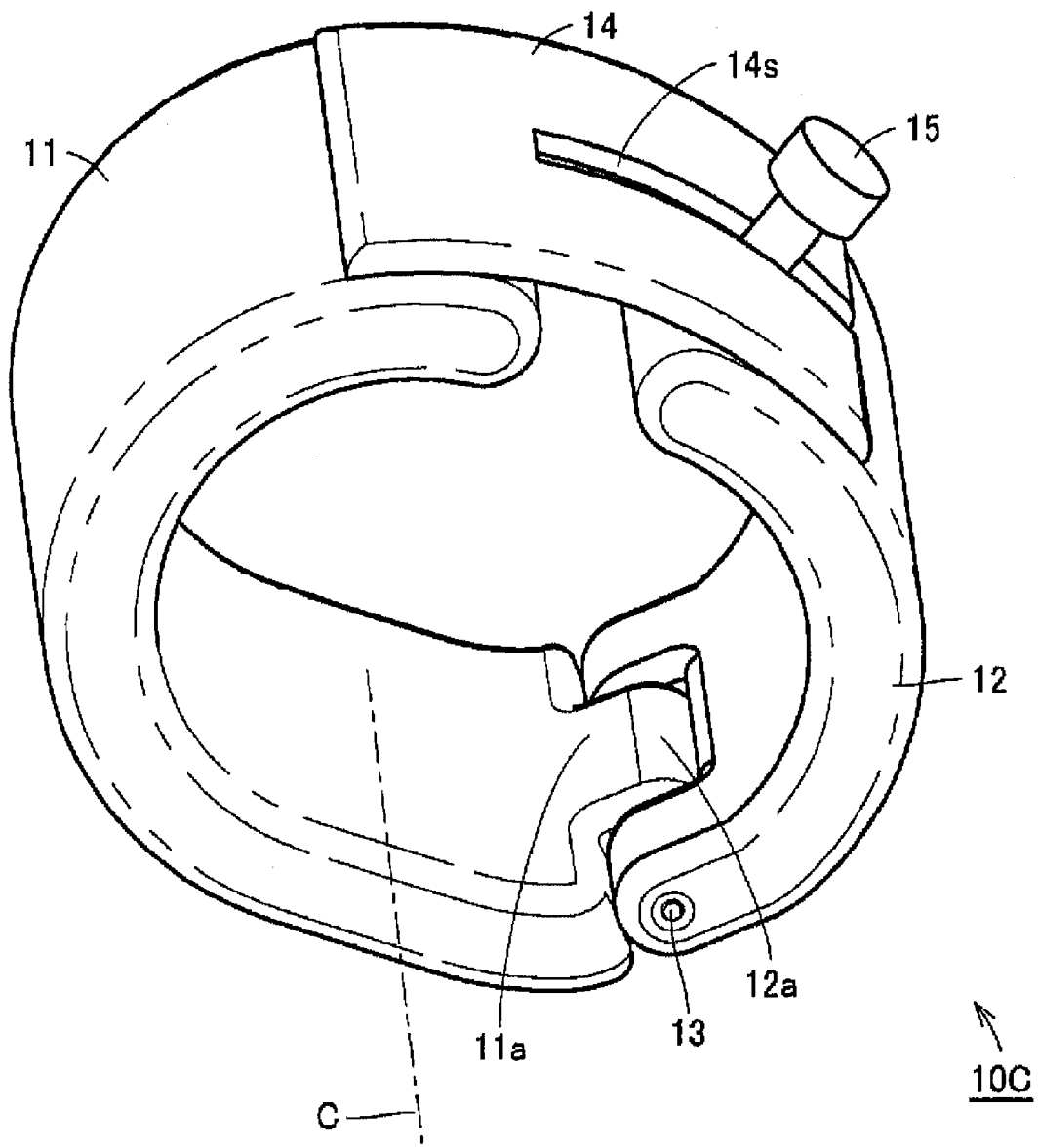
FIG. 5 is a whole perspective view showing only the structure of the fixing member 10C of the cuff of the wrist-mount blood pressure monitor according to the third embodiment of the present invention.

Since the characteristic of the cuff of the wrist-mount blood pressure monitor in this embodiment is the structure of the fixing member, only the structure of the fixing member will be explained. The other parts of the structure are the same as the structure of the cuff of the wrist-mount blood pressure monitor 10 in the first embodiment. The structure of the fixing member 10C will be explained below with reference to FIG. 5. FIG. 5 is a whole perspective view showing the structure of the fixing member 10C.

(Structure of the Fixing Member 10C)

When the fixing member 10C in this embodiment is compared with the structure of the fixing member 10A in the first embodiment, the connected position of the first half split ring-shaped fixing tool 11 and the second half split ring-shaped fixing tool 12 by means of the hinge 13 shifts from an axial center C. The other parts of the structure are the same as the structure of the fixing member 10A.

(Working Effect)

Also the cuff of the wrist-mount blood pressure monitor using the fixing member 10C in this embodiment can produce the working effect similar to that of the first embodiment.

Fourth Embodiment

Figure 6:
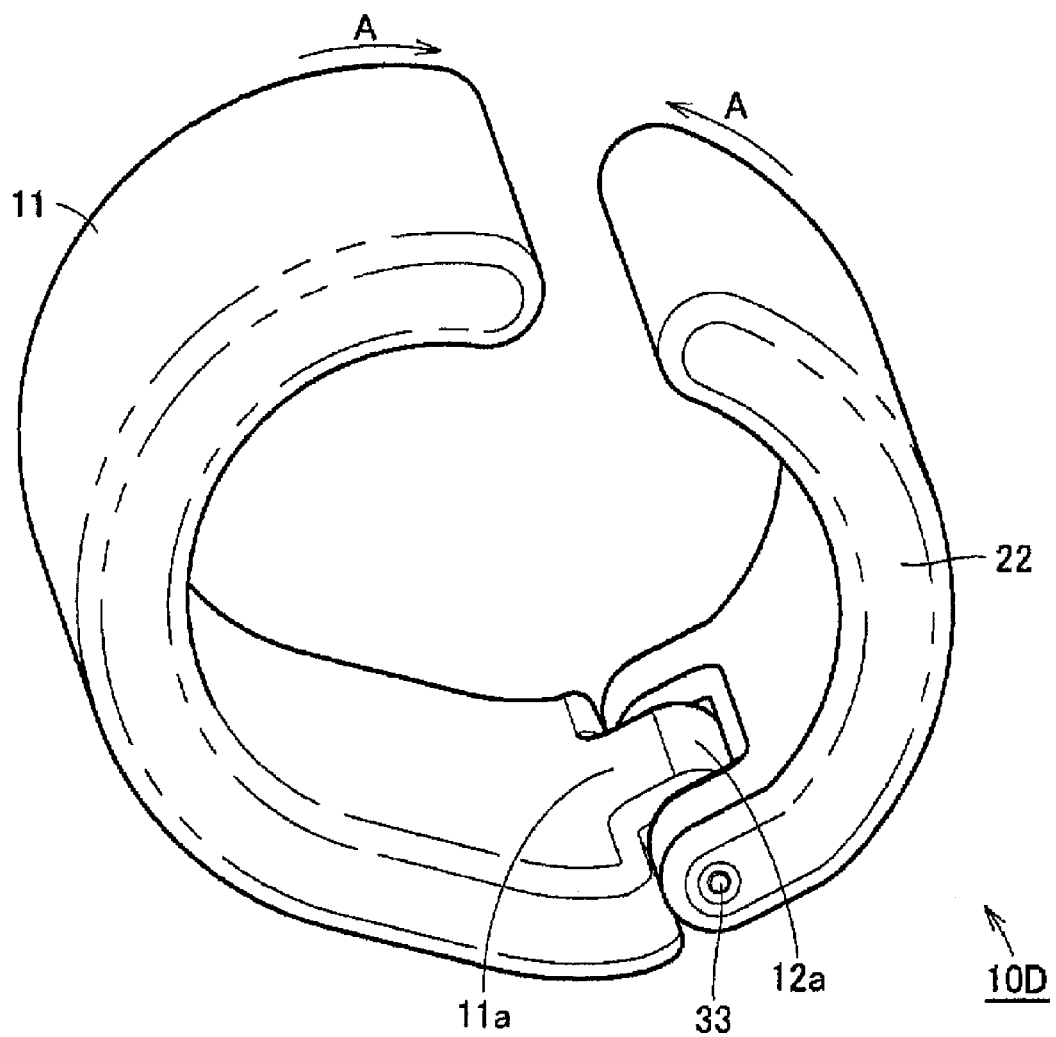
FIG. 6 is a whole perspective view showing only the structure of the fixing member 10D of the cuff of the wrist-mount blood pressure monitor according to the fourth embodiment of the present invention.

Since the characteristic of the cuff of the wrist-mount blood pressure monitor in this embodiment is the structure of the fixing member, only the structure of the fixing member will be explained. The other parts of the structure are the same as the structure of the cuff of the wrist-mount blood pressure monitor 10 in the first embodiment. The structure of the fixing member 10D will be explained below with reference to FIG. 6. FIG. 6 is a whole perspective view showing the structure of the fixing member 10D.

(Structure of the Fixing Member 10D)

When the fixing member 10D in this embodiment is compared with the structure of the fixing member 10A in the first embodiment, a hinge 33 containing a spring member, which connects the first half split ring-shaped fixing tool 11 and the second half split ring-shaped fixing tool 12, is used instead of the rail 14 and the clamping screw 15 as the clamper for clamping the fixing member 10D to the wrist (to a direction of an arrow A in the drawing) in a state where the fixing member 10D is mounted on the wrist. The other parts of the structure are the same as the structure of the fixing member 10A.

(Working Effect)

Also the cuff of the wrist-mount blood pressure monitor using the fixing member 10D in this embodiment can produce the working effect similar to that of the first embodiment. In this embodiment, when the gap between the first half split ring-shaped fixing tool 11 and the second half split ring-shaped fixing tool 12 is tried to be widened, the spring member in the hinge 33 always applies an energizing force to a a direction in which the first half split ring-shaped fixing tool 11 and the second half split ring-shaped fixing too 112 are closed (to the direction A in the drawing). As a result, the mounting work for mounting the fixing member 10D on the wrist can be facilitated.

Fifth Embodiment

Figure 7:
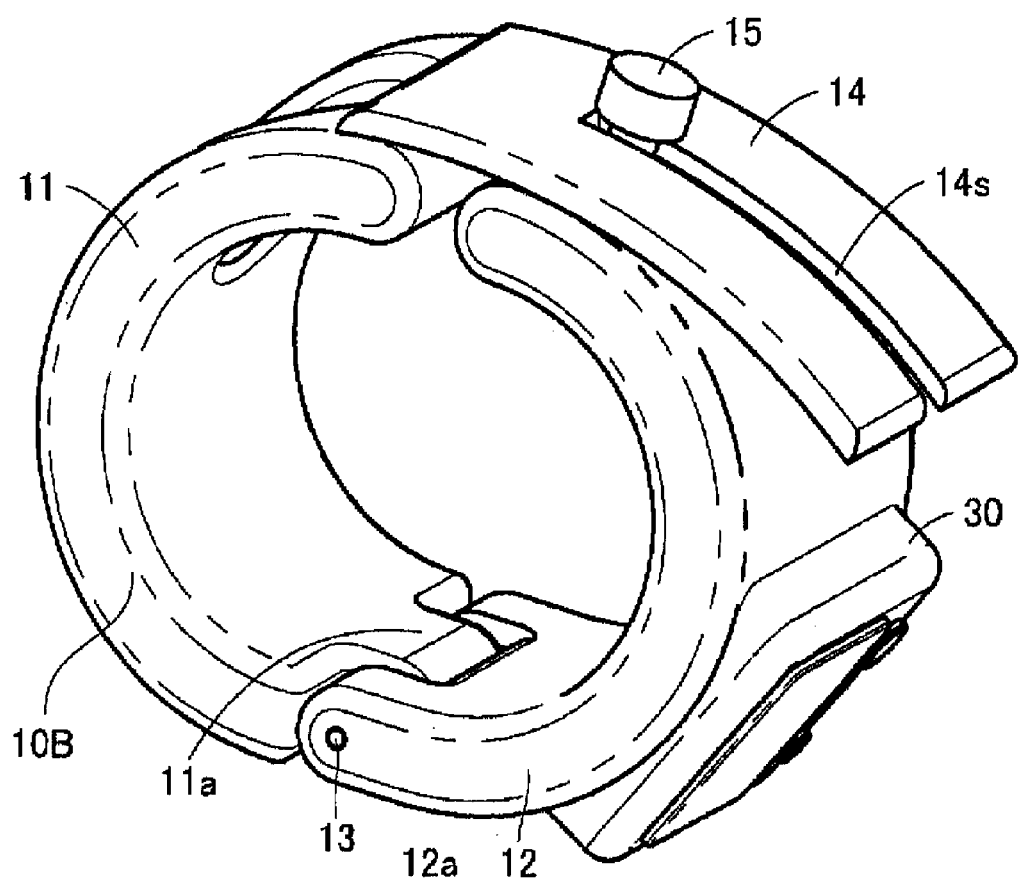
FIG. 7 is a whole perspective view showing a structure in which a main body portion 30 of the wrist-mount blood pressure monitor is mounted on the fixing member 10B of the second embodiment according to the fifth embodiment of the present invention.

In this embodiment, as shown in FIG. 7, a main body section 30 of the wrist-mount blood pressure monitor is mounted onto the fixing tool 10B in the second embodiment.

In the cuff of the wrist-mount blood pressure monitor 10 in the second embodiment, since the capacity of the inflatable bag 16 can be miniaturized, the necessary air flow rate can be reduced, so that the miniaturization of the air pump can be realized. As a result, as shown in FIG. 7, the main body section 30 can be thinned, and thus the entire wrist-mount blood pressure monitor to which the cuff of the wrist-mount blood pressure monitor 10 is applied can be miniaturized.

The present invention can be applied not only to the fixing member 10B of the second embodiment but also to the fixing member 10A of the first embodiment and the fixing member 10C of the third embodiment.

Sixth Embodiment

Figure 8:
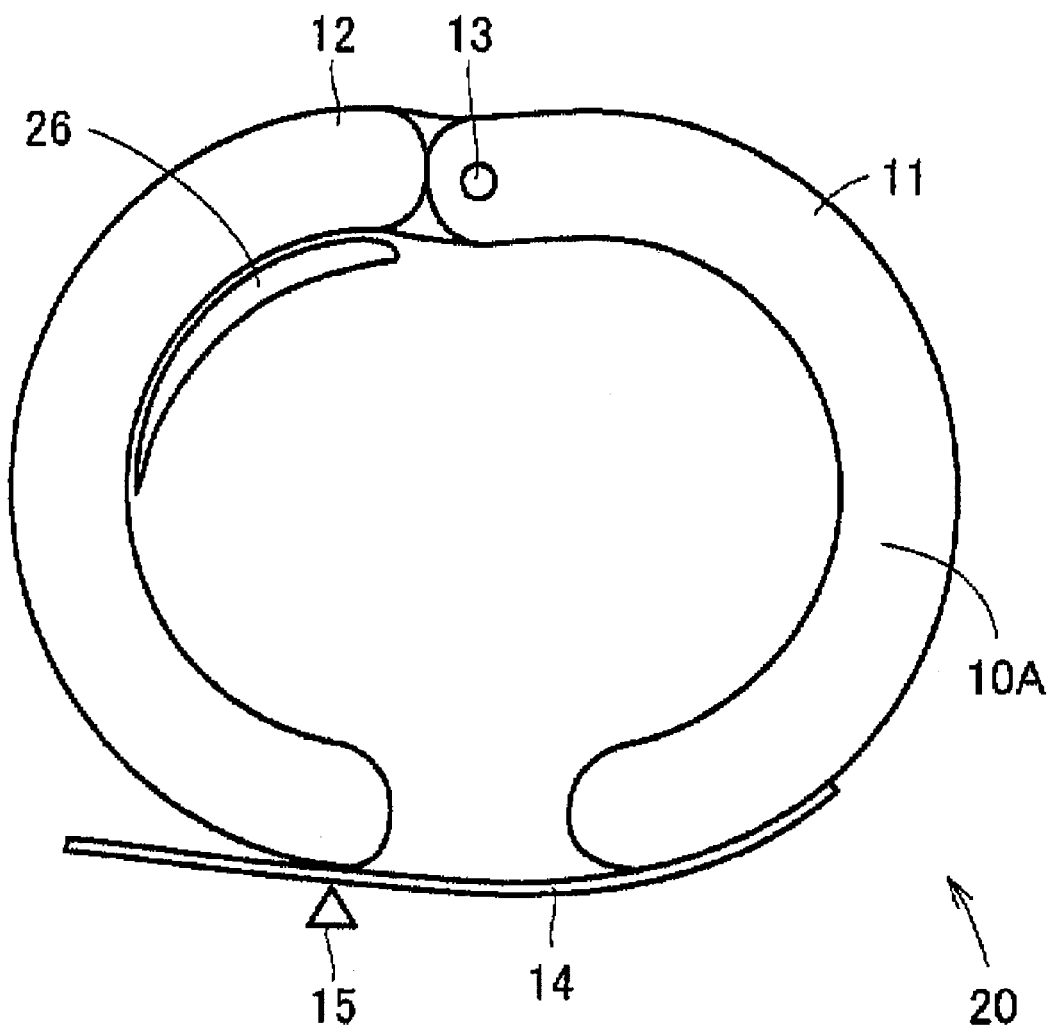
FIG. 8 is a sectional view showing a structure of the cuff of the wrist-mount blood pressure monitor 20 according to the sixth embodiment of the present invention.

The characteristic of the cuff of the wrist-mount blood pressure monitor in this embodiment is arrangement of the inflatable bag. In the cuff of the wrist-mount blood pressure monitor 10 in the first through fifth embodiments, as shown in FIG. 1, the inflatable bag 16 is arranged over an entire area of the inner surface of the fixing member 10A. In the cuff of the wrist-mount blood pressure monitor 20 in this embodiment, however, as shown in FIG. 8, the inflatable bag 26 is provided only on a selected area of the inner surface of the fixing member 10A.

Figure 9B:
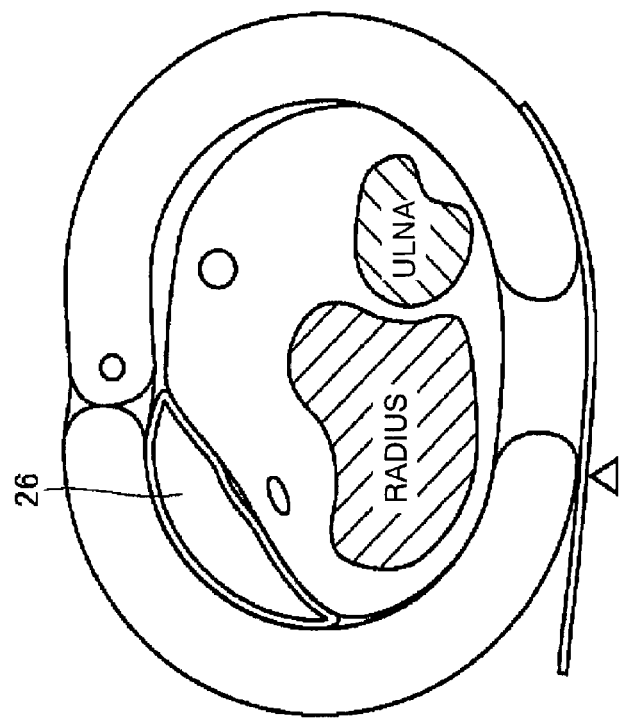
FIGS. 9A and 9B are diagrams showing a state where the cuff of the wrist-mount blood pressure monitor 20 is mounted on the wrist 101 according to the sixth embodiment of the present invention.
Figure 9A:
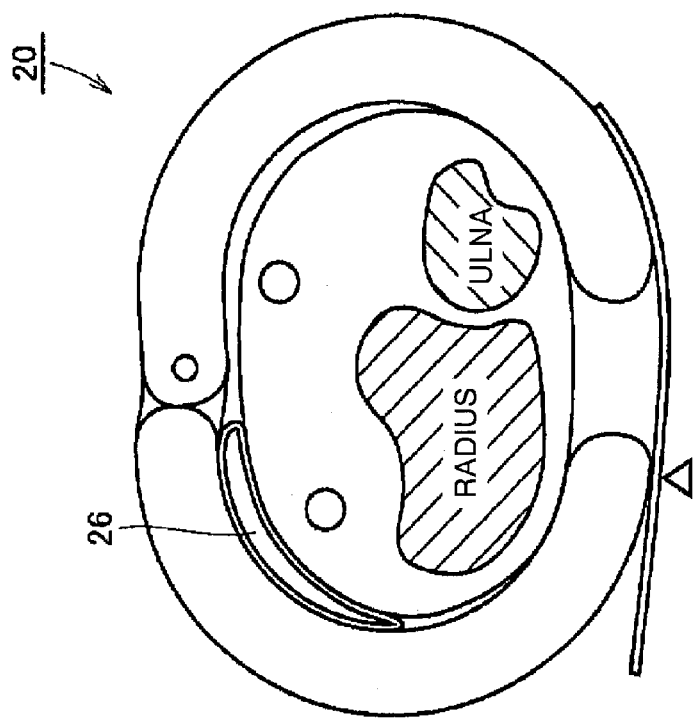

FIGS. 9A and 9B show a state where the cuff of the wrist-mount blood pressure monitor 20 having the above structure is mounted on the wrist 101. FIG. 9A shows the state before the inflatable bag 26 inflates, and FIG. 9B shows the state where the inflatable bag 26 inflates.

In this embodiment, as mentioned above, the most part of the pressing force caused by the expansion of the inflatable bag can contribute to the pressing force of artery. As shown in the drawing, therefore, when only the radial artery 104 is tried to be pressed, the inflatable bag 26 is provided only on the selected area corresponding to the radial artery 104, so that only the radial artery 104 can be pressed securely. As a result, even in the case where the extremely small pressing fluid bag 26 presses locally, the blood pressure can be measured accurately. The necessary air flow rate for the inflatable bag 26 can be further reduced, so that the miniaturization of the air pump can be realized. The above embodiments explain the case in which the first half split ring-shaped fixing tool 11 and the second half split ring-shaped fixing tool 12 are used, but the similar working effect can be produced also by one unit type ring-shaped member having an opening area which overall has the similar shape and can allow the wrist to pass. The present invention is not limited to the two split structure composed of the first half split ring-shaped fixing tool 11 and the second half split ring-shaped fixing tool 12, and can adopt also a two or more split structure.

The above disclosed embodiments are, therefore, examples at all points and does not become the basis of limiting interpretation. The technical scope of the present invention is not, therefore, interpreted only by the above embodiments but is defined based on the claims. The present invention includes all modifications in meaning equivalent to the claims and within the scope of the claims.

According to the cuff of the wrist-mount blood pressure monitor based on the present invention, the miniaturization of the air pump can be realized. As a result, the whole wrist-mount blood pressure monitor to which the cuff of the wrist-mount blood pressure monitor is applied can be miniaturized. When the expansion quantity of the inflatable bag is reduced, the tension to be generated in the inflatable bag is suppressed to be small, so that the accurate measurement of the blood pressure can be also realized.

The invention claimed is:

1. A cuff of a wrist-mount blood pressure monitor comprising:
   an inflatable bag to which a predetermined quantity of fluid is supplied in order to press on an artery of a wrist; and
   a fixing member seperate from the inflatable bag for mounting the inflatable bag on the wrist,
   wherein the fixing member comprises a substantially ring-shaped fixing tool having an opening end including a predetermined gap area, holding the inflatable bag on an inner side of the fixing tool, and having rigidity for preventing elastic deformation in a state where the inflatable bag is inflated; and a clamp for mounting the fixing tool on the wrist, and
   wherein the fixing tool comprises first and second half split ring-shaped fixing tools connected at one end of each of said half split ring-shaped fixing tools so as to be turnable relatively to each other and the opening end is configured to be positioned on a back side of the wrist, wherein free ends of the first half split ring-shaped fixing tool and the second half ring shaped fixing tool are each configured to come into contact with a radius and an ulna.

2. The cuff of a wrist-mount blood pressure monitor according to claim 1, wherein the fixing tool has an opening formed therein that is shaped to receive the wrist without making contact with a corresponding processus styloideus ulnae on an inner surface of said fixing tool.

3. The cuff of a wrist-mount blood pressure monitor according to claim 1, wherein
   the inflatable bag is provided only on a selected area on the inner surface of the fixing tool.

* * * * *